US00PP33873P2

(12) United States Plant Patent
Sheehan

(10) Patent No.: US PP33,873 P2
(45) Date of Patent: Jan. 18, 2022

(54) GRAPEVINE PLANT NAMED 'SHEEGENE 104'

(50) Latin Name: *Vitis vinifera*
Varietal Denomination: Sheegene 104

(71) Applicant: SNFL Australia Pty Ltd., Victoria (AU)

(72) Inventor: Timothy P. Sheehan, Vancouver, WA (US)

(73) Assignee: SNFL Australia Pty Ltd., Victoria (AU)

( * ) Notice: Subject to any disclaimer, the term of this patent is extended or adjusted under 35 U.S.C. 154(b) by 0 days.

(21) Appl. No.: 17/118,303

(22) Filed: Dec. 10, 2020

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

(56) References Cited

PUBLICATIONS

U.S. Appl. No. 17/117,438, filed Dec. 10, 2020, Coetzee.
U.S. Appl. No. 17/117,451, filed Dec. 10, 2020, Coetzee.

*Primary Examiner* — Keith O. Robinson
(74) *Attorney, Agent, or Firm* — Dentons US LLP

(57) ABSTRACT

'Sheegene 104' is a new and distinct grapevine plant with novel characteristics that include good fertility and naturally loose bunches, nice and well-structured. The berries produced by 'Sheegene 104' are black and seedless with a crisp texture and neutral flavor and no detectable seed traces. The berries produced by 'Sheegene 104' are large, weighing 8-9 g/berry on average, and harvested between September and October in Spain (Murcia Region).

1 Drawing Sheet

Latin name of the genus and species of the plant claimed: *Vitis vinifera.*

Cultivar denomination: 'Sheegene 104'.

BACKGROUND OF THE INVENTION

The present invention relates to a new distinct variety of seedless grapevine named 'Sheegene 104'. The variety originated from a hybridization performed in Mildura, Victoria, Australia during 2002 between 'Crimson Seedless' (unpatented), as the pollen parent, and 'Autumn Royal' (unpatented), as the seed parent. Abortive seed traces were embryo cultured and the resulting plant was planted in an evaluation block during 2004. The first evaluation of the fruit produced by 'Sheegene 104' was performed during 2007. 'Sheegene 104' was first asexually propagated by field grafting dormant hardwood scions to rootstock (1103 Paulsen Rootstock; unpatented) in 2010 in Irymple, Victoria, Australia. Fruit from the resulting four grafted 'Sheegene 104' vines was first harvested in 2012. All characteristics and distinctions remain true to form and are established and transmitted through succeeding propagations.

SUMMARY OF THE INVENTION

The following are the most outstanding and distinguishing characteristics of 'Sheegene 104'. 'Sheegene 104' produces large, black (5RP 3/2), seedless berries that are harvested between September-October, in Murcia-Spain and weigh on average 8-9 g/berry.

'Sheegene 104' can be distinguished from its male parent, 'Crimson Seedless', in that the new cultivar produces blackcolored grapes while 'Crimson Seedless' produces red (2.5R 5/10) grapes. Additionally, 'Sheegene 104' clusters are heavier than 'Crimson Seedless' clusters (average 902 g v. 650 g) and the average weight of 'Sheegene 104' berries is also greater than 'Crimson Seedless' berries (average 8.2 g v. 4 g).

'Sheegene 104' is believed to be most similar to 'Autumn Royal'. Nonetheless, the new cultivar can be distinguished from its female parent, 'Autumn Royal', in that 'Sheegene 104' berries are heavier than 'Autumn Royal' (8.2 g v. 6.5 g); 'Autumn Royal' has 2 to 4 rudimentary seeds per berry while 'Sheegene 104' rudimentary (aborted) seeds are not detectable; 'Sheegene 104' berries are also more strongly attached to the pedicel than 'Autumn Royal'. Additionally, 'Sheegene 104' exhibits high vigour compared to 'Autumn Royals' medium to low vigour.

'Sugrathirteen' (U.S. Plant Pat. No. 10,434) is a well-known black seedless commercial variety. 'Sheegene 104' can be distinguished from 'Sugrathirteen' based at least upon berry shape, berry size, and time of berry ripening. Berries produced by 'Sheegene 104' exhibit an ovoid shape, whereas berries produced by 'Sugrathirteen' exhibit a long elliptic shape. 'Sheegene 104' berries are heavier than 'Sugrathirteen' berries (8.2 g v. 4.7 g). Additionally, 'Sheegene 104' is a late ripening variety (end September), whereas 'Sugrathirteen' its an early ripening variety (July).

'Sheegene 104' is harvested between September and October in Murcia, Spain, which is later than the early September harvest period of 'Autumn Royal' and the early July harvest period of 'Sugrathirteen'.

BRIEF DESCRIPTION OF THE DRAWING

FIG. 1—Shows the form, foliage, and fruit of a 4-year-old 'Sheegene 104' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'Sheegene 104'. The detailed description was obtained between March and November using 4-year-old plants grown in the field in Murcia, Spain. The color references are to the Munsell Plant Tissue Color Book, 2012 Edition by Munsell Color.

Classification:

*Family*.—Vitaceae.

*Botanical*.—*Vitis vinifera*.

*Common name*.—Grapevine.

*Cultivar name*.—'Sheegene 104'.

Plant:

*Plant habit and growth*.—Semi-erect/horizontal.

*Age at maturity*.—4 years old.

*Size* (*at maturity*).—Height: 225 cm. Width: 300 cm.

*Vigor*.—Medium to high.

*Productivity*.—High.

*Rootstock*.—Name of rootstock: 1103 Paulsen Rootstock (unpatented). Age of rootstock at time of grafting: one year old.

Trunk:

*Size*.—Height:151 cm. Diameter: 8.5 cm.

*Surface texture*.—Smooth.

*Bark color*.—Exterior: 7.5YR 6/2. Interior: 7.5YR 6/6.

Canes:

*Size*.—Diameter: 11 mm. Length: 200 cm. Surface texture (mature cane): very finely ribbed. Surface texture (inmature cane): smooth.

*Form* (*woody shoot cross section form*).—Pith in center with diaphragm at the nodes.

*Color*.—Mature: 7.5YR 7/6 at 5 months. Immature: 2.5GY 8/6 at 4 weeks.

*Internode length* (*upper mature sun cane*).—13.3 cm.

Time of bud burst: 50% bud break by March 28.

Tendrils:

*Form*.—Mostly trifid and bifid.

*Size*.—Medium/long.

*Length*.—24.6 cm.

*Diameter*.—3 mm.

*Texture and distribution of tendril at each node beginning at base*.—Smooth and discontinuous; 000000101001111 (0 means no tendril at that node and 1 means there is tendril at the node).

*Color*.—Mature: 5GY 7/8 at 4 weeks. Immature: 2.5GY 8/10 at 10 days.

*Anthocyanin*.—Mature: absent. Immature: 2.5YR 6/8.

Growing tips (young shoot):

*Pubescence*.—Absent.

*Color*.—2.5GY 7/8.

*Anthocyanin*.—Present, 5YR 6/8.

*Shape*.—Half open.

*Apex*.—Triangular.

Leaves:

*Shape*.—Cuneiform.

*Apex*.—Pointed.

*Base*.—Rounded.

*Number of lobes*.—5.

*Margin*.—Irregular teeth.

*Length of teeth on margin*.—2-10 mm.

*Shape of teeth on margin*.—Most slightly convex, some straight.

*Texture* (*mature leaf*).—Upper surface: smooth, flat, slightly bullate along veins. Lower surface: smooth, glabrous.

*Size*.—Immature: Length: 5.1 cm at 10 days. Width: 6.8 cm at 10 days. Mature: Length: 13.4 cm at 4 weeks. Width: 18.9 cm at 4 weeks.

*Color, immature leaf*.—Upper surface: 5GY 6/6; anthocyanin 2.5YR 5/8. Lower surface: 5GY 6/8; anthocyanin 2.5YR 5/8.

*Color, mature leaf*.—Upper surface: 5GY 5/6. Lower surface: 5GY 6/8.

*Venation*.—Pattern: primary veins on upper surface are flat; veins on lower surface are raised, there is some pubescence along veins close to base. Color: Upper surface: 5GY 7/8. Lower surface: 2.5GY 8/8.

*Petiolar sinus*.—V-shaped that are half open.

*Petiole*.—Length: 13.5 cm. Diameter: 3.7 mm. Color: 2.5GY 7/8.

Floral cluster:

*General description and location*.—Mostly on $3^{rd}$ to $6^{th}$ node.

*Quantity of inflorescences per cluster*.—225.

*Size*.—Length: 14.3 cm. Width: 9.1 cm (spread); 6.2 cm (hanging).

*Peduncle length*.—3.3 cm.

*Inflorescences*.—Hermaphroditic.

*Stamens*.—Straight, length 2.2 mm.

*Anthers*.—Small and nondescript.

*Date of bloom*.—Start of bloom, May 8; and 100% bloom, May 16.

*Pollen amount and color*.—Sparse, yellow (5Y 8/10).

*Calyptra*.—5 segments with complete separation.

*Calyptra color*.—5GY 5/6.

Fruit:

*Time of year of commercial harvest and shipment*.—Late season, between September and October, in Murcia Region, Spain.

*Cluster* (*primary bunches*).—General size: large (902 g tipped and 1175 g not tipped). Length (without peduncle): 18.2 cm tipped and 23.7 cm not tipped. Width: 18.2 cm (hanging), 29.4 cm (spread). Density: medium. Peduncle: Length: 4.3 cm. Diameter: 7.0 mm. Color: 5GY 7/8. Number of berries per cluster: 110 tipped and 143 not tipped. Berry: Size: large (8.2 g). Diameter: 20.7 mm. Length: 29.8 mm. Shape: ovoid. Uniformity: uniform. Brix content: 17.3° Brix. Skin color: blue/black when mature, 5RP 3/2; red when partially mature, 2.5R 4/6. Pedicel: Length: 7.4 mm. Diameter: 1.6 mm. Color: 5GY 7/8. Strength of attachment to berry: medium.

*Cluster* (*secondary bunches*).—General size: small (93.4 g). Length (without peduncle): 7.6 cm. Width: 7.5 cm (hanging), 11.1 cm (spread). Density: medium. Peduncle: Length: 8.9 cm. Diameter: 2.7 mm. Color: 2.5GY 8/8. Number of berries per cluster: 18. Berry: Size: medium (4.7 g). Diameter: 18 mm. Length: 22.6 mm. Shape: ovoid. Uniformity: uniform. Brix content: 19.9° brix. Skin color: 5RP 3/2. Pedicel: Length: 6.2 mm. Diameter: 1.7 mm. Color: 2.5 GY 8/8. Strength of attachment to berry: medium.

Berry flesh:

*Color*.—2.5GY 7/4.

*Juice color*.—2.5Y 8/2, cloudy beige-yellow.

*Juice production*.—Medium, 14% wt/wt.

*Thickness of skin*.—Medium.

*Flavor*.—Sweet neutral flavor, with a good brix levels and low acidity; very balanced flavor.

*Fragrance*.—Sweet neutral, with hints of green apple.

*Texture*.—Crisp.

*Seeds*.—Seed rudiments not detectable.

*Use*.—Fresh table.

Disease and insect resistance: This cultivar is susceptible to the main diseases of its species, such as *Erysiphe necator, Plasmopara viticola, Botrytis cinerea, Daktulosphaira vifoliae, Ceratitis capitata, Planococcus ficus, Planococcus citri, Empoasca vitis*.

What is claimed is:

1. A new and distinct variety of grapevine plant named 'Sheegene 104' as shown and described herein.

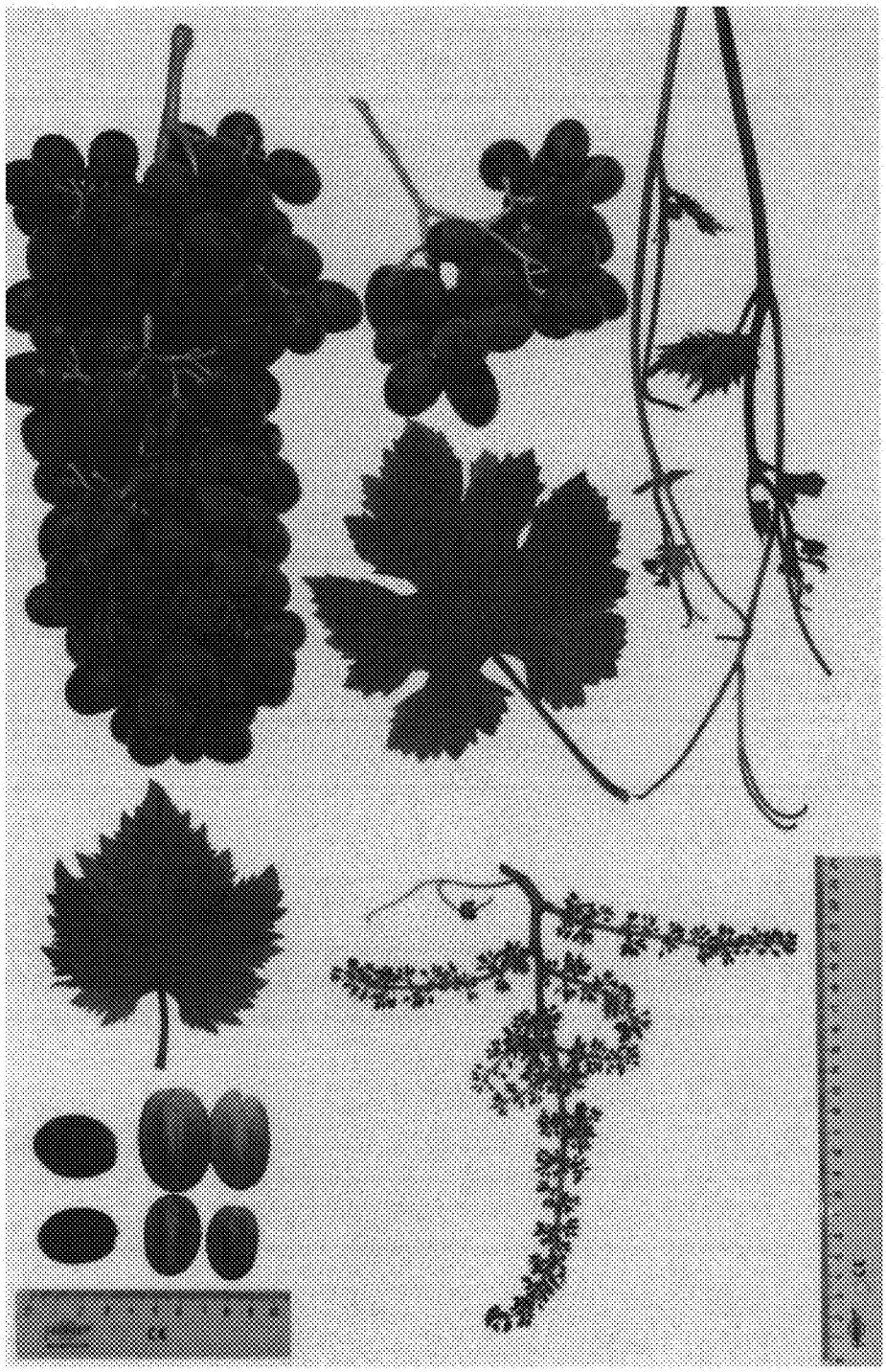

* * * * *